(12) United States Patent
Huang et al.

(10) Patent No.: US 9,946,341 B2
(45) Date of Patent: Apr. 17, 2018

(54) INFORMATION OBSERVATION METHOD AND INFORMATION OBSERVATION DEVICE

(71) Applicant: BEIJING ZHIGU RUI TUO TECH CO., LTD., Beijing (CN)

(72) Inventors: Weicai Huang, Beijing (CN); Hanning Zhou, Beijing (CN)

(73) Assignee: BEIJING ZHIGU RUI TUO TECH CO., LTD., Beijing (CN)

( * ) Notice: Subject to any disclaimer, the term of this patent is extended or adjusted under 35 U.S.C. 154(b) by 58 days.

(21) Appl. No.: 14/787,745

(22) PCT Filed: Jan. 22, 2014

(86) PCT No.: PCT/CN2014/071130
§ 371 (c)(1),
(2) Date: Oct. 28, 2015

(87) PCT Pub. No.: WO2015/035745
PCT Pub. Date: Mar. 19, 2015

(65) Prior Publication Data
US 2016/0070345 A1 Mar. 10, 2016

(30) Foreign Application Priority Data
Sep. 16, 2013 (CN) .......................... 2013 1 0419430

(51) Int. Cl.
*A61B 3/14* (2006.01)
*G06F 3/01* (2006.01)
(Continued)

(52) U.S. Cl.
CPC ................ *G06F 3/013* (2013.01); *A61B 3/12* (2013.01); *G06F 3/0481* (2013.01)

(58) Field of Classification Search
CPC ................ G06F 3/013; G06F 3/04842; G06F 17/30873; A61B 3/12; A61B 3/113; A61B 5/165; G06K 9/00604
(Continued)

(56) References Cited

U.S. PATENT DOCUMENTS

2004/0218827 A1 11/2004 Cohen et al.
2006/0122531 A1 6/2006 Goodall et al.
(Continued)

FOREIGN PATENT DOCUMENTS

CN 101311882 A 11/2008
CN 101356078 A 1/2009
(Continued)

OTHER PUBLICATIONS

Huang Qiao, "The eye track technique and the HCI system based on gaze input," China Great Master's Theses Full-text Database (Information Science and Technology Set), 2008, No. 09, 74 pages.
(Continued)

*Primary Examiner* — Mustak Choudhury

(57) ABSTRACT

The present application discloses an information observation method and an information observation apparatus, and relates to the field of multimedia information processing technologies. The method comprises: detecting a position of a sightline focusing point of an observer; in response to that it is detected that the sightline focusing point of the observer moves away from an observed object, judging whether the observer has observed all important information on the observed object; and in response to that it is judged that the observer has not observed all important information on the observed object, reminding the observer. For the method and the apparatus in embodiments of the present application, from the perspective of an actual observation behavior of an observer, a position of a sightline focusing point of the
(Continued)

observer is detected to determine an observation behavior of the observer for important information, so as to radically prevent missing of important information.

13 Claims, 6 Drawing Sheets

(51) Int. Cl.
  *A61B 3/12* (2006.01)
  *G06F 3/0481* (2013.01)
(58) Field of Classification Search
  USPC ............ 351/206, 209, 210, 246; 348/333.01, 348/E05.022; 704/235, E15.043; 715/802
  See application file for complete search history.

(56) References Cited

U.S. PATENT DOCUMENTS

2010/0026871 A1* 2/2010 Yonaha .................... H04N 5/76
                                                    348/333.01
2010/0039618 A1* 2/2010 De Lemos ............. A61B 3/113
                                                    351/209

FOREIGN PATENT DOCUMENTS

| CN | 101548546 | | 9/2009 |
|---|---|---|---|
| CN | 101893934 | A | 11/2010 |
| CN | 102708358 | A | 10/2012 |
| CN | 102945128 | A | 2/2013 |
| CN | 103190883 | A | 7/2013 |
| JP | 2010-039646 | A | 2/2010 |

OTHER PUBLICATIONS

Office Action for CN App. No. 201310419430.2, dated Mar. 15, 2016, 8 pages.

PCT International Search Report dated Jun. 11, 2014, issued in corresponding International Application No. PCT/CN2014/071130 (8 pages).

Office Action for Chinese Application No. 201310419430.2, dated Mar. 16, 2017, (with English Translation), 13 pages.

* cited by examiner

INFORMATION OBSERVATION METHOD AND INFORMATION OBSERVATION DEVICE

CROSS-REFERENCE TO RELATED APPLICATIONS

This application is a national stage application of International Application No. PCT/CN2014/071130, filed on Jan. 22, 2014, which claims priority to and the benefit of Chinese Patent Application No. 201310419430.2, filed with the State Intellectual Property Office of P.R. China on Sep. 16, 2013, and entitled "INFORMATION OBSERVATION METHOD AND INFORMATION OBSERVATION DEVICE". The contents of both of the above-referenced applications are herein incorporated by reference in their entirety.

BACKGROUND

Technical Field

The present application relates to the field of multimedia information processing technologies, and in particular, to an information observation method and an information observation apparatus.

Background

Researches show that when human eyes look at a certain object (comprising a person, a scenery, an article, a picture, an image displayed on a computer, and the like), even if there is sufficient time, in most cases, people will not notice every detail of the object and inevitably, often ignore important content. For example, in viewing a financial statement having a large quantity of data, it is not very easy for people to notice certain critical data from the large quantity of data.

To prevent an observer from missing important information, there is in the prior art a method of attracting the sight of an observer by extracting an important part from an image, highlighting the important part, and changing the color of an important area, and the like, thereby reducing a probability of missing of important information.

However, such a method only increases the probability of preventing missing of important information, but fails to radically prevent a possibility of missing of important information.

SUMMARY

An objective of the present application is to provide an information observation method and an information observation apparatus, so that missing of important information can be prevented radically.

To achieve the foregoing objective, in a first aspect, an embodiment of the present application provides an information observation method, and the method comprises:

detecting a position of a sightline focusing point of an observer;

in response to that it is detected that the sightline focusing point of the observer moves away from an observed object, judging whether the observer has observed all important information on the observed object; and in response to that it is judged that the observer has not observed all important information on the observed object, reminding the observer.

In a second aspect, an embodiment of the present application provides an information observation apparatus, and the apparatus comprises:

a detection module, configured to detect a position of a sightline focusing point of an observer;

a judgment module, configured to: in response to that it is detected that the sightline focusing point of the observer moves away from an observed object, judge whether the observer has observed all important information on the observed object; and a reminding module, configured to: in response to that the judgment module judges that the observer has not observed all important information in the observed object, remind the observer.

In a third aspect, an embodiment of the present application provides a computer readable storage medium, wherein the computer readable storage medium comprises an executable instruction, and when a central processing unit of an information observation apparatus executes the executable instruction, the executable instruction is configured to cause the information observation apparatus to execute the following method:

detecting a position of a sightline focusing point of an observer;

in response to that it is detected that the sightline focusing point of the observer moves away from an observed object, judging whether the observer has observed all important information on the observed object; and in response to that it is judged that the observer has not observed all important information on the observed object, reminding the observer.

In a fourth aspect, an embodiment of the present application provides an information observation apparatus, comprising a central processing unit and a memory, wherein the memory stores a computer execution instruction, and the central processing unit is connected to the memory through a communication bus, and when the information observation apparatus runs, the central processing unit executes the computer execution instruction stored in the memory, to cause the information observation apparatus to execute the following method:

detecting a position of a sightline focusing point of an observer;

in response to that it is detected that the sightline focusing point of the observer moves away from an observed object, judging whether the observer has observed all important information on the observed object; and in response to that it is judged that the observer has not observed all important information on the observed object, reminding the observer.

For the method and apparatus in the embodiments of the present application, from the perspective of an actual observation behavior of an observer, a position of a sightline focusing point of the observer is detected to determine an observation behavior of the observer for important information, so as to radically prevent missing of important information.

DETAILED DESCRIPTION

The following further describes specific embodiments of the present application in detail with reference to accompanying drawings and the embodiments. The following embodiments are used to describe the present application, but are not used to limit a scope of the present application.

A process in which a human eye clearly images a target object on a retina when looking at the object is referred to as focusing of the eye. Accordingly, a clearest imaging point on the retina is a sightline focusing point when the human eye looking at the target object.

In the embodiments of the present application, an observed object may be any visual information such as any text information and multimedia information, and may have a conventional paper carrier or be displayed on any device having a display function.

Figure 1:
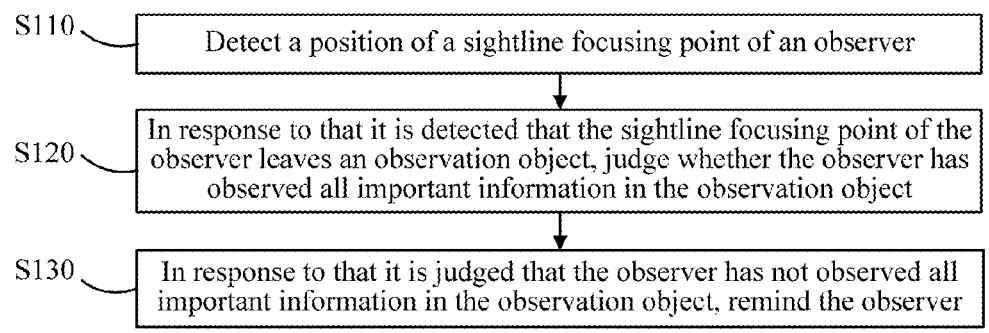
FIG. 1 is a flowchart of an information observation method according to an embodiment of the present application.

As shown in FIG. 1, an embodiment of the present application provides an information observation method, and the method comprises:

S110. Detection step: Detect a position of a sightline focusing point of an observer.

S120. Judgment step: In response to that it is detected that the sightline focusing point of the observer moves away from an observed object, judge whether the observer has observed all important information on the observed object.

S130. Reminding step: In response to that it is judged that the observer has not observed the important information on the observed object, remind the observer.

For the method in the embodiment of the present application, from the perspective of an actual observation behavior of an observer, a position of a sightline focusing point of the observer is detected to determine an observation behavior of the observer for important information, so as to radically prevent missing of important information.

In the method in the embodiment of the present application, there may be multiple manners of detecting a position of a sightline focusing point of an observer, for example:

a) Pupil-corneal reflection vector method. An eyeball image is obtained by using a camera, a pupil in the eyeball image is extracted, and the coordinates of a center position of the pupil are obtained, which indicate the position of a sightline. Refer to "A new sightline tracking method based on a pupil-corneal reflection technology"—CHINESE JOURNAL OF COMPUTERS, Vol. 33, Issue 7, July 2010.

b) Electrooculography (EOG) method. Two pairs of silver chloride electrodes for skin surface are placed separately on left and right sides and upper and lower sides of an eye, and a weak electrical signal in an eyeball changing direction is caused. After the weak electrical signal is amplified, position information of eyeball movement is obtained, and the sightline of the eye is deduced. Refer to "A lead mode for EOG collection"—COMPUTER TECHNOLOGY AND DEVELOPMENT C(MPUTEI), Vol. 19, Issue 6.

c) Iris-sclera border method. Two infrared photodiodes are installed near an ocular region. An infrared light is used to illuminate the ocular region. When an eyeball moves to the left or to the right, changes occur in infrared rays received by the two infrared photodiodes. An eye movement can be detected by using this differential signal. Refer to "A detection device in an eye movement tracking system"—COMPUTER AND DIGITAL ENGINEERING, Issue 3, 2007.

d) Corneal reflection method. When an eyeball moves, light is illuminated on a cornea at a changed angle, so that reflected light in a different direction is obtained. A virtual image formed on a surface of the cornea moves due to rolling of the eyeball. A position of the image is detected in real time, and after signal processing, an eye movement signal may be obtained. Refer to "A detection device in an eye movement tracking system"—COMPUTER AND DIGITAL ENGINEERING, Issue 3, 2007.

e) Dual Purkinje image method. Refer to "FreeGaze: a gaze tracking system for everyday gaze interaction"—ETRA '02 Proceedings of the 2002 symposium on Eye tracking research & applications.

f) Contact lens method. A reflector is fixed on a cornea or a sclera and reflects a fixed light beam to a different direction when an eyeball moves, so as to acquire an eye movement signal. Refer to "Development of fish-eye VR system with human visual function and biological signal" by Y. Kuno, T. Yagi, Y. Uchikawa, in: IEEE Internat. Conf. on Multi-sensor Fusion and Integration for Intelligent Systems, 1996, pp. 389 to 394.

g) According to an optical parameter of an optical path between an image capture position and an eye of an observer when a clearest image presented on an imaging surface of the eye is captured, a position of a sightline focusing point of the eye is obtained. Such a manner may have the highest detection accuracy, and when this manner is used, Step S110 may further comprise:

S111. Collect an image presented by a fundus of an eye of an observer.

S112. Adjust an imaging parameter of an optical path between the eye of the observer and a capture position, until at least one image that meets at least one predetermined definition standard, for example, the clearest image, is captured.

S113. Process the obtained image, and calculate a position of a focusing point according to the imaging parameter of the optical path between the eye of the observer and the capture position in response to that the at least one image that meets the predetermined definition standard is captured (for example, when the clearest image is collected) and at least one optical parameter of the eye, where the optical parameter of the eye comprises an eye optical axis direction.

By processing an image of the fundus of an eye, an optical parameter of the eye when the clearest image is captured is obtained, so that the position of the current focusing point of the eye can be calculated, providing a basis for further detection of an observation behavior of an observer based on the precise position of the focusing point.

The image presented by the "fundus" herein is mainly an image presented on a retina, which may be an image of the fundus itself, or may be an image of another thing that is cast onto the fundus.

In Step S112, by adjusting a focal length of an optical component in the optical path between the eye and the capture position and/or the position of the optical component in the optical path, the at least one image that meets at least one predetermined definition standard may be acquired when the optical component is at a certain position or in a certain state. The adjustment may be continuous and real-time adjustment.

The standard for clarity herein may be set according to a measurement parameter for clarity that is frequently used by a person skilled in the art, for example, a parameter such as an effective resolution of the image, which is no longer described herein.

In a possible implementation in the method in the embodiment of the present application, the optical component may be a focal-length adjustable lens, configured to complete the adjustment of the focal length of its own by adjusting the refractive index and/or shape of the optical component. Specifically, 1) the focal length is adjusted by adjusting the curvature of at least one surface of the focal-length adjustable lens, for example, adjusting the curvature of the focal-length adjustable lens by increasing or decreasing the liquid medium in a cavity formed by a double-layer transparent layer; 2) the focal length is adjusted by changing the refractive index of the focal-length adjustable lens, for example, filling a specific liquid crystal medium in the focal-length adjustable lens, and adjusting the arrangement mode of the liquid crystal medium by adjusting the voltage of a corresponding electrode of the liquid crystal medium, thereby changing the refractive index of the focal-length adjustable lens.

In another possible implementation in the method in the embodiment of the present application, the optical component may be a lens set, configured to complete the adjustment of the focal length of the lens set by adjusting the relative positions between lenses of the lens set.

In addition to the foregoing two ways of changing the optical path parameters of the system by adjusting the characteristics of the optical component, the optical path parameters of the system can further be changed by adjusting the position of the optical component in the optical path.

In addition, in the method in the embodiment of the present application, Step S113 further comprises:

S1131. Analyze the image obtained in Step S111 to find the clearest image.

S1132. Calculate an optical parameter of an eye according to the clearest image and the known imaging parameter when the clearest image is obtained.

The adjustment in Step S112 causes to obtain the clearest image; however, Step S113 is needed to find the clearest image, and the optical parameter of an eye can be calculated according to the clearest image and the known optical path parameters.

Figure 2A:
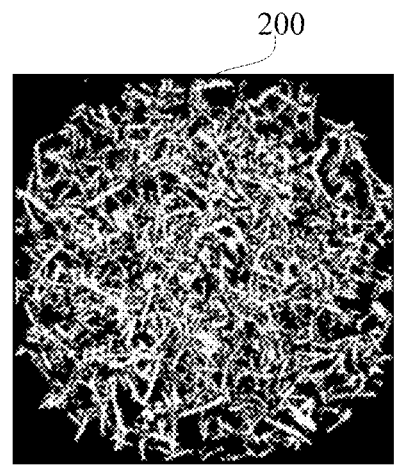
FIG. 2(a) is an exemplary diagram of a light spot pattern.
Figure 2B:
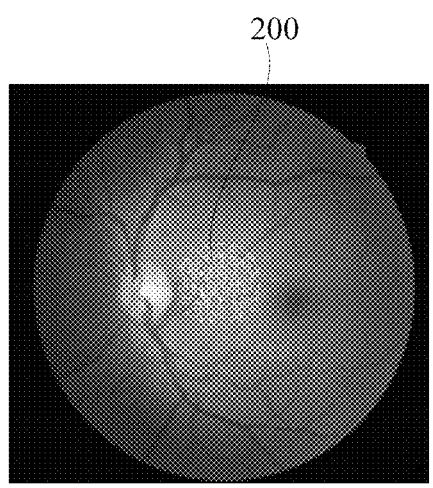
FIG. 2(b) is an image of a fundus of an observer collected when there is projection of the light spot pattern shown in FIG. 2(a) in a method in an embodiment of the present application.

In the method in the embodiment of the present application, Step S113 may further comprise:

S1133. Cast a light spot to the fundus. The cast light spot may have no specific pattern and is only used for illuminating the fundus. The cast light spot can further include a pattern with abundant features. The abundant features of a pattern can facilitate the detection and enhance the detection precision. FIG. 2(a) is an exemplary diagram of a light spot pattern 200, and the pattern can be formed by a light spot pattern generator, for example, frosted glass; FIG. 2(b) shows an image of the fundus captured when the light spot pattern 550 is cast thereon.

In order not to affect the normal viewing of an eye, preferably, the light spot is an infrared light spot which is invisible to the eye. In this case, in order to reduce the interference from other spectra, a step of filtering out light, other than that through an eye-invisible light transmission filter, in the cast light spot.

Correspondingly, the method in the embodiment of the present application may further comprise:

S1134. Control the brightness of the cast light spot according to the result obtained through analysis in Step S1131. The result of analysis includes the contrast of image features, texture features, and the like.

A special circumstance of controlling the brightness of the cast light spot is to start or stop the cast. For example, the cast can be stopped periodically when an observer gazing at one point; and when the fundus of an observer is bright enough, the cast can be stopped and the distance from the current sightline focusing point of an eye to the eye can be detected by using the information about the fundus.

Furthermore, the brightness of the cast light spot can also be controlled according to the ambient light.

In the method in the embodiment of the present application, Step S113 may further comprise:

S1135. Calibrate an image of the fundus to obtain at least one reference image corresponding to the image presented by the fundus. Specifically, the captured image and the reference image are compared and calculated to obtain the clearest image. Here, the clearest image can be an image obtained with a minimum difference from the reference image. In this implementation, the difference between the currently obtained image and the reference image is calculated by means of an existing image processing algorithm, for example, by using a classical phase difference automatic focusing algorithm.

The optical parameter of an eye obtained in Step S1132 may comprise the eye optical axis direction obtained according to the features of the eye when the clearest image is obtained. The features of an eye herein can be acquired from the clearest image or can also be acquired otherwise. The eye optical axis direction represents the gaze direction of the sightline of the eye. Specifically, the eye optical axis direction can be obtained by means of the features of a fundus when the clearest image is obtained. The accuracy of determining the eye optical axis direction by means of the features of the fundus is higher.

When a light spot pattern is cast to the fundus, the size of the light spot pattern may be larger than a visible area of the fundus or smaller than that of, wherein:

when the area of the light spot pattern is smaller than or equal to that of the visible area of the fundus, the optical axis direction of an eye can be determined by detecting the position of the light spot pattern on a detected image relative to the fundus by using a classical feature point matching algorithm (for example, the scale invariant feature transform (SIFT) algorithm);

when the area of the light spot pattern is greater than or equal to that of the visible area of the fundus, the eye optical axis direction can be determined by means of the position of the light spot pattern on the obtained image relative to an original light spot pattern (obtained through image calibration), so as to determine the direction of the sightline of a user.

In another possible implementation of the embodiment of the present application, the eye optical axis direction may also be obtained according to the features of the eye pupil when the clearest image is obtained. The features of the eye pupil herein can be acquired from the clearest image, and can also be acquired otherwise. The obtaining of the optical axis direction of an eye by means of the features of the eye pupil is available in the prior art, which is no longer described herein.

In addition, in a possible implementation of the embodiment of the present application, a step of calibrating the eye optical axis direction can be further comprised, so as to determine the eye optical axis direction more accurately.

In the method of the embodiment of the present application, the known imaging parameter comprises a fixed imaging parameter and a real-time imaging parameter, wherein the real-time imaging parameter is the parameter information about the optical component when a clearest image is acquired, and the parameter information can be obtained by recording in real time when the clearest image is acquired.

After the current optical parameter of an eye is obtained, the distance from a focusing point of the eye to the eye can be calculated (the specific process is described in detail in combination with the apparatus part):

By detecting the position of the sightline focusing point of the observer, in Step S120, when it is detected that the sightline focusing point of the observer moves out of an area corresponding to the observed object for a first preset period of time, it is judged that the sightline focusing point of the observer moves away from the observed object. The area corresponding to the observed object is preset; or may be set according to content of the observed object, for example, an area corresponding to a specific paragraph; or may also be set according to the area of the observed object; for example, for paper reading, the area may be a page, while for electronic reading, the area may be an display area of the electronic reading or a displayed page of the electronic reading. The first preset period of time may be set according to an actual situation, for example, according to a scenario in which the observer is and/or the size of the area of the observed object, and the like, so as to exclude a case in which the sightline focusing point moves outside the area of the observed object due to a subconscious action of the observer, for example, a blink, a transient head action, and the like.

In Step S120, when it is detected that the observed object changed, it is judged that the sightline focusing point of the observer moves away from the observed object. The switching of the observed object refers to a change, triggered by the observer or triggered automatically, of the observed object, and is, for example, page turning, page scrolling, and the like.

For one observed object, there may be more than one piece or more than one place of important information. When the sightline focusing point of the observer moves away from the observed object, it needs to be determined whether the observer has traversed all important information. In the method in the embodiment of the present application, when the position of the sightline focusing point of the observer falls within an area corresponding to the important information for a second preset period of time or a preset number of times, it may be judged that the observer has observed the corresponding important information. The second preset period of time and the preset number of times may also be set according to an actual situation, as long as a possibility that an unintentional sightline focusing point of the observer falls within the area corresponding to the important information is excluded.

In addition, the method in the embodiment of the present application may further comprise:

S140. Identify all important information in the observed object.

Before or when the position of the sightline focusing point of the observer is detected, the important information in the observed object needs to be identified. The important information may be identified according to the content of the observed object; for example, content that needs special attention is identified semantically; or the observed object has visual features for the important information or the area corresponding to the important information, for example, a special sign for the important information or the area corresponding to the important information, a text, an image, a font, a color, a layout feature, and the like at this position, and the important information is identified by using these visual features. The important information may also be identified according to metadata of the observed object. The metadata is data that describes data and an environment of the data. In the method in the embodiment of the present application, the metadata is description information of the observed object and may be generated in a process of generating the observed object, and the metadata describes which areas in the observed object comprise the important information. The metadata of the observed object can be obtained by the observer.

After the important information of the observed object is identified, to fully attract attention of the observer during observation, the method in the embodiment of the present application further comprises a step of marking the important information; for example, the important information or the area corresponding to the important information may be marked through processing such as boldfacing, blackening, underlining, and highlighting of the corresponding area.

In addition, in detecting the position of the sightline focusing point of the observer, the method in the embodiment of the present application further comprises a step of labeling important information, which has been observed by the observer, in the observed object. Specifically, after the observer has observed a certain piece of important information and/or an area corresponding to the important information, the observer may remove the original mark at the important information and/or the area corresponding to the important information, and label the important information and/or the area corresponding to the important information in a manner of a visual mark different from the original mark. When no mark exists at the important information and/or the area corresponding to the important information, the important information and/or the area corresponding to the important information may further be labeled in a manner of labeling with a visual mark. In view of the above, when the observer finds that there is missed important information, the important information that has been observed can be filtered out more efficiently.

In Step S130, the observer may be reminded in one or several of the following manners: an audio manner, in which a reminder tone is output to remind the observer that there is important information that has not be viewed; a visual manner, in which the observer may be reminded in a manner (for example, flickering) visible to the observer that there is important information that has not be viewed, or the observer may be reminded more directly and efficiently by visually labeling (distinguished from a mark that has been made for the important information and/or the important information that has been observed) important information that has not been observed; a touch manner, for example, protrusion; a vibration manner; and a manner of restricting an operation of the observer, in which, specifically, when an observation behavior occurs on a device having a display function, the observer is reminded, in a manner of prohibiting the observer from scrolling or turning a page, and the like, that there is important information that has not been observed.

For the method in the embodiment of the present application, a position of a sightline focusing point of an observer is detected accurately, and an observation behavior of the observer is detected according to a position of a focusing point, so that missing of important information can be radically prevented; in addition, all/observed/unobserved important information is labeled, so as to further improve efficiency of the observer to observe important information.

In the various embodiments of the present application, sequence numbers of the foregoing processes do not indicate a specific execution sequence. The execution sequence of the processes should be determined according to functions and an internal logic of the processes, but should not constitute any limitation on an implementation process of the embodiments of the present application.

Figure 3:
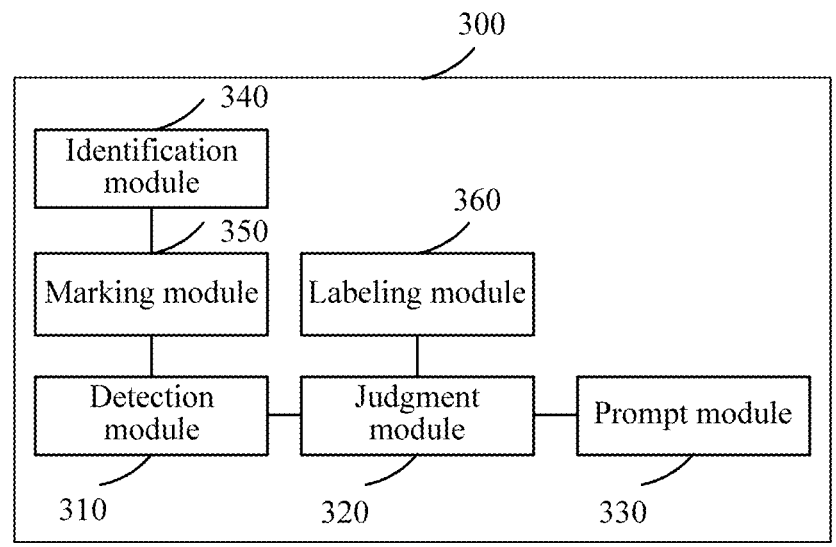
FIG. 3 is a schematic structural diagram of an information observation apparatus according to an embodiment of the present application.

As shown in FIG. 3, an embodiment of the present application further provides an information observation apparatus 300. The apparatus may be an independent device that is owned or worn by an observer, or is partially owned or worn by the observer. When an observed object is displayed on a device having a display function, the apparatus in the embodiment of the present application further partially or completely belongs to the device. As shown in FIG. 3, the information observation apparatus 300 in the embodiment of the present application comprises:

a detection module 310, configured to detect a position of a sightline focusing point of the observer;

a judgment module 320, configured to: in response to that the detection module 310 detects that the sightline focusing point of the observer moves away from an observed object, judge whether the observer has observed all important information on the observed object; and a reminding module 330, configured to: in response to that the judgment module 320 judges that the observer has not observed all important information on the observed object, remind the observer.

For the apparatus in the embodiment of the present application, from the perspective of an actual observation behavior of an observer, a position of a sightline focusing point of an observer is detected to determine an observation behavior of the observer for important information, so as to radically prevent missing of important information.

In the apparatus in the embodiment of the present application, a manner in which the detection module 310 detects a position of a sightline focusing point of an observer may be any one of a) to g) that are mentioned in the method embodiment shown in FIG. 1. In the apparatus in the embodiment of the present application, the manner g) with the highest detection accuracy is used, and correspondingly, the detection module 310 may be any of the focusing point detection systems that are shown in FIG. 4(a) to FIG. 4(d), FIG. 5, and FIG. 6.

Figure 4A:
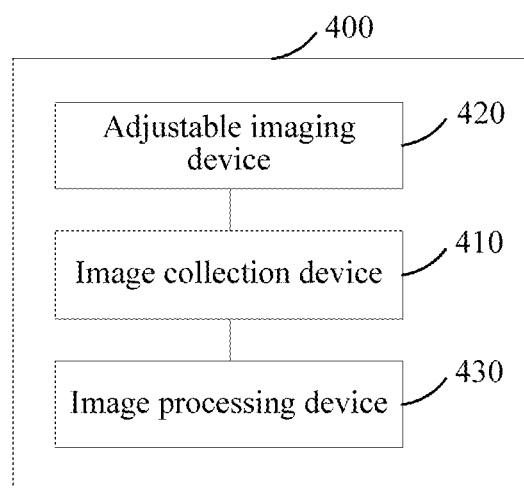
FIG. 4(a) is a structural block diagram of an eye focusing point detection system of an information observation apparatus according to an embodiment of the present application.

As shown in FIG. 4(a), the focusing point detection system 400 comprises:

an image capture device 410, configured to capture an image presented by a fundus of an eye;

an adjustable imaging device 420, configured to adjust an imaging parameter of an optical path between the eye and the image capture device 410, until the image capture device 410 capture s at least one image that meets at least one predetermined definition standard, for example, a clearest image; and an image processing device 430, configured to process the image obtained by the image capture device 410, and calculate the position of the focusing point of the eye according to the imaging parameter of the optical path between the image capture device 410 and the eye in response to that the at least one image that meets at least one predetermined definition standard is captured (for example, when the clearest image is obtained) and at least one optical parameter of the eye.

The system 400, by processing an image of the fundus of an eye, obtains an optical parameter of the eye when the image capture device has obtained at least one image that meets at least one predetermined definition standard, so that the position of the focusing point of the eye can be calculated, providing a basis for further detection of an observation behavior of an observer based on the precise position of the focusing point.

Figure 4B:
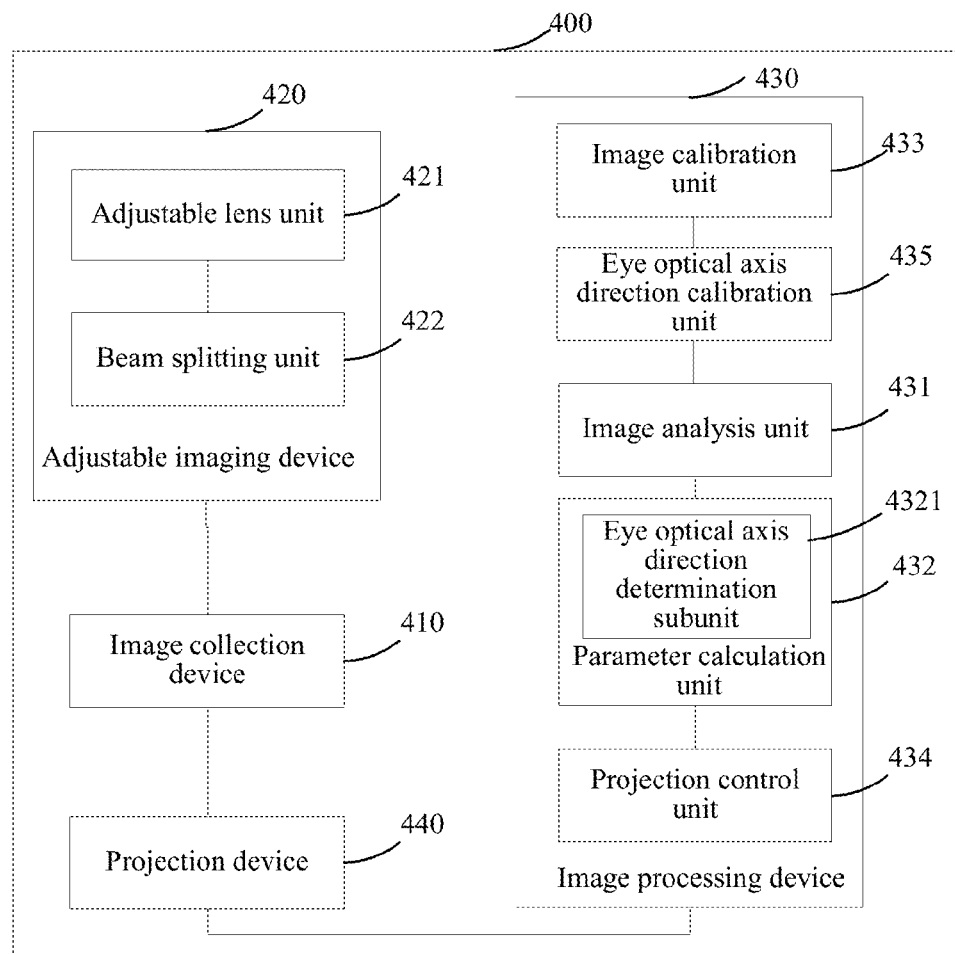
FIG. 4(b) is another structural block diagram of an eye focusing point detection system of an information observation apparatus according to an embodiment of the present application.

As shown in FIG. 4(b), in a possible implementation, the image capture device 410 is a micro camera, and in another possible implementation of the embodiment of the present application, the image capture device 410 can also directly use a photosensitive imaging device, such as a CCD device or a CMOS device, and the like.

As shown in FIG. 4(b), in a possible implementation, the adjustable imaging device 420 comprises an adjustable lens unit 421, located in the optical path between an eye and the image collection device 410, with the focal length thereof being adjustable and/or the position thereof in the optical path being adjustable. The equivalent focal length of the system between an eye and the image collection device 410 is enabled to be adjustable by means of the adjustable lens unit 421, and the adjustable lens unit 421 is adjusted to cause the image capture device 410 to obtain at least one clearest image that meets at least one predetermined definition standard at a certain position or in a certain state of the adjustable lens unit 421. In this implementation, the adjustable lens unit 421 can be adjusted continuously in real time during detection.

In a possible implementation, the adjustable lens unit 421 is a focal-length adjustable lens, configured to complete the adjustment of the focal length of its own by adjusting the refractive index and/or shape of its own. Specifically, 1) the focal length is adjusted by adjusting the curvature of at least one surface of the focal-length adjustable lens, for example, adjusting the curvature of the focal-length adjustable lens by increasing or decreasing the liquid medium in a cavity formed by a double-layer transparent layer; 2) the focal length is adjusted by changing the refractive index of the focal-length adjustable lens, for example, filling a specific liquid crystal medium in the focal-length adjustable lens, and adjusting the arrangement mode of the liquid crystal medium by adjusting the voltage of a corresponding electrode of the liquid crystal medium, thereby changing the refractive index of the focal-length adjustable lens.

In another possible implementation, the adjustable lens unit 421 comprises: a lens set, configured to complete the adjustment of the focal length of the lens set by adjusting the relative positions between lenses of the lens set.

In addition to the foregoing two ways of changing the optical path parameters of the system by adjusting the characteristics of the adjustable lens unit 421, the optical path parameters of the system can further be changed by adjusting the position of the adjustable lens unit 421 on the optical path.

In addition, in order not to affect the viewing experience of an observer to an observed object, and in order to enable a system to be portably applied to a wearable device, the adjustable imaging device 420 may further comprise: a beam splitting unit 422, configured to form a light transfer path between an eye and the observed object and between the eye and the image capture device 410. In this way, an optical path can be folded to reduce the volume of a system, and at the same time, other visual experiences of a user are not affected as much as possible.

The beam splitting unit 422 may comprise: a first beam splitting subunit located between an eye and an observed object, and configured to transmit the light from the observed object to the eye and transferring the light from the eye to an image capture device. The first beam splitting subunit can be a beam splitter, a beam splitting optical waveguide (comprising an optical fiber) or other suitable beam splitting apparatuses.

In addition, the image processing device 430 may comprise: an optical path calibration unit, configured to calibrate the optical path of the system, for example, align and calibrate the optical axis of the optical path, and the like, to ensure the precision of measurement.

an image analysis unit 431, configured to analyze an image obtained by the image capture device to find the clearest image; and a parameter calculation unit 432, configured to calculate an optical parameter of an eye according to the clearest image and the known imaging parameter of the system when the clearest image is obtained.

In this implementation, the adjustable imaging device 420 is enabled to obtain a clearest image by means of the image capture device 410, but it needs to find the clearest image by means of the image analysis unit 431, and then, the optical parameter of an eye can be calculated according to the clearest image and the known optical path parameters of the system.

In a possible implementation, the system 400 may further comprise: a casting device 440, configured to cast a light spot to the fundus. The function of the casting device 440 can be achieved by means of a micro projector. The light spot cast herein can have no specific pattern and be merely used for illuminating the fundus. The cast light spot can further include a pattern with abundant features. The abundant features of a pattern can facilitate the detection and enhance the detection precision. A light spot pattern 550 is shown in FIG. 2(*a*), and an image of the fundus captured when there is a light spot pattern is shown in FIG. 2(*b*).

In order not to affect the normal viewing of an eye, the light spot can be an infrared light spot which is invisible to the eye. In this case, in order to reduce the interference from other spectra:

an emergent surface of the projection device 440 can be provided with an eye-invisible light transmission filter; and an incident surface of the image capture device 410 is provided with an eye-invisible light transmission filter.

In a possible implementation, the image processing device 430 may further comprise:

a cast control unit 434 configured to control the brightness of the light spot cast by the casting device 440 according to a result obtained by the image analysis unit 431.

For example, the projection control unit 434 can adaptively adjust the brightness according to the characteristics of an image obtained by the image collection device 410. The characteristics of an image herein include the contrast of image features, texture features, and the like.

A special circumstance of controlling the brightness of the light spot cast by the casting device 440 is to turn on or turn off the casting device 440. For example, the casting device 440 can be turned off periodically when an observer continuously fixes on one point; when the fundus of an observer is bright enough, a light emitting source can be turned off and the distance from the current sightline focusing point of an eye to the eye can be detected by only using the information about the fundus.

Furthermore, the cast control unit 434 can also control the brightness of the light spot cast by the casting device according to the ambient light.

In a possible implementation, the image processing device 430 may further comprise: an image calibration unit 433, configured to calibrate an image of the fundus to obtain at least one reference image corresponding to the image presented on the fundus.

The image analysis unit 431 compares an image obtained by the image collection device 430 and the reference image and calculates same to obtain the clearest image. Here, the clearest image can be an image obtained having a minimum difference from the reference image. In this implementation, the difference between the currently obtained image and the reference image is calculated by means of an existing image processing algorithm, for example, by using a classical phase difference automatic focusing algorithm.

In a possible implementation, the parameter calculation unit 432 comprises:

an eye optical axis direction determination subunit 4321, configured to obtain the eye optical axis direction according to the features of the eye when the clearest image is obtained, where the features of an eye herein can be acquired from the clearest image, or can also be acquired otherwise. The eye optical axis direction represents the gaze direction of the sightline of the eye.

In a possible implementation, the eye optical axis direction determination subunit 4321 comprises: a first determination portion, configured to obtain the eye optical axis direction according to the features of the fundus when the clearest image is obtained. Compared with obtaining the eye optical axis direction by means of the features of the pupil and the eyeball surface, the accuracy of obtaining the eye optical axis direction by means of the features of the fundus is higher.

When a light spot pattern is cast to the fundus, the size of the light spot pattern may be larger than a visible area of the fundus or smaller than that of, wherein:

when the area of the light spot pattern is smaller than or equal to that of the visible area of the fundus, the optical axis direction of an eye can be determined by detecting the position of the light spot pattern on a detected image relative to the fundus by using a classical feature point matching algorithm (for example, the SIFT algorithm);

when the area of the light spot pattern is greater than or equal to that of the visible area of the fundus, the eye optical axis direction can be determined by means of the position of the light spot pattern on the obtained image relative to an original light spot pattern (obtained by an image calibration unit), so as to determine the direction of the sightline of a user.

In another possible implementation, the eye optical axis direction determination subunit 4321 comprises: a second determination portion, configured to obtain the eye optical axis direction according to the features of the eye pupil when the clearest image is obtained. The features of the eye pupil herein can be acquired from the clearest image, and can also be acquired otherwise. The obtaining of the optical axis direction of an eye by means of the features of the eye pupil is available in the prior art, which is no longer described herein.

In a possible implementation, the image processing device 430 further comprises: an eye optical axis direction calibration unit 435, configured to calibrate the eye optical axis direction to determine the eye optical axis direction more accurately.

In this implementation, the known imaging parameter of the system comprises a fixed imaging parameter and a real-time imaging parameter, wherein the real-time imaging parameter is the parameter information about the adjustable lens unit when a clearest image is acquired, and the parameter information can be obtained by recording in real time when the clearest image is acquired.

Figure 4C:
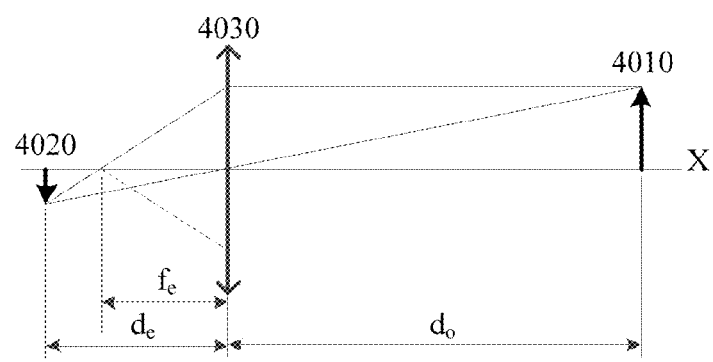
FIG. 4(c) is a schematic diagram of an optical path of eye imaging of the eye focusing point detection system of an information observation apparatus according to an embodiment of the present application.

After the current optical parameter of an eye is obtained, the distance from a focusing point of the eye to the eye can be calculated, which is specifically as follows:

FIG. 4(c) is a schematic diagram of eye imaging, and Equation (1) can be obtained from FIG. 4(c) in combination with the lens imaging equation in the classical optical theory:

$$\frac{1}{d_o} + \frac{1}{d_e} = \frac{1}{f_e} \quad (1)$$

where $d_o$ and $d_e$ are the distance from a current observed object 4010 of an eye to an eye equivalent lens 4030 and the distance from a real image 4020 on the retina to the eye equivalent lens 4030 respectively, $f_e$ is the equivalent focal length of the eye equivalent lens 4030, and X is the eye optical axis direction (that is, the optical axis of the sightline).

Figure 4D:
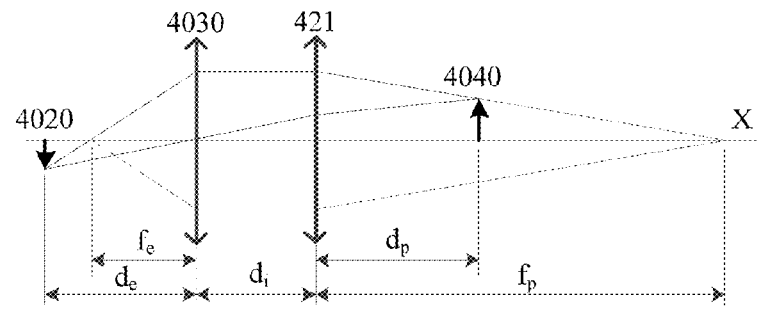
FIG. 4(d) is a schematic diagram in which an eye focusing point detection system of an information observation apparatus obtains the distance from a focusing point of an eye to the eye according to a known imaging parameter of the system and an optical parameter of the eye according to an embodiment of the present application.

FIG. 4(d) is a schematic diagram where the distance from the focusing point of an eye to the eye is obtained according to the known optical parameter of the system and the optical parameter of the eye. In FIG. 4(d), a light spot 4040 forms a virtual image (not shown) via an adjustable lens unit 421, and by assuming the distance of the virtual image from the adjustable lens unit 421 to be x, in combination with Equation (1), the following system of equations can be obtained:

$$\begin{cases} \dfrac{1}{d_p} - \dfrac{1}{x} = \dfrac{1}{f_p} \\ \dfrac{1}{d_i + x} + \dfrac{1}{d_e} = \dfrac{1}{f_e} \end{cases} \quad (2)$$

where $d_p$ is the optical equivalent distance from the light spot 4040 to the adjustable lens unit 421, $d_i$ is the optical equivalent distance from the adjustable lens unit 421 to the eye equivalent lens 4030, $f_p$ is the focal length value of the adjustable lens unit 421, and $d_i$ is the distance from the eye equivalent lens 4030 to the adjustable lens unit 421.

The distance $d_o$ from the current observed object 4010 (the focusing point of the eye) to the eye equivalent lens 4030 can be obtained as shown in Equation (3) from (1) and (2):

$$d_o = d_i + \frac{d_p \cdot f_p}{f_p - d_p} \quad (3)$$

According to the distance from the observed object 4010 to the eye calculated above, and the eye optical axis direction which can be obtained as a result of the preceding description, the position about the focusing point of the eye can be obtained easily.

Figure 5:
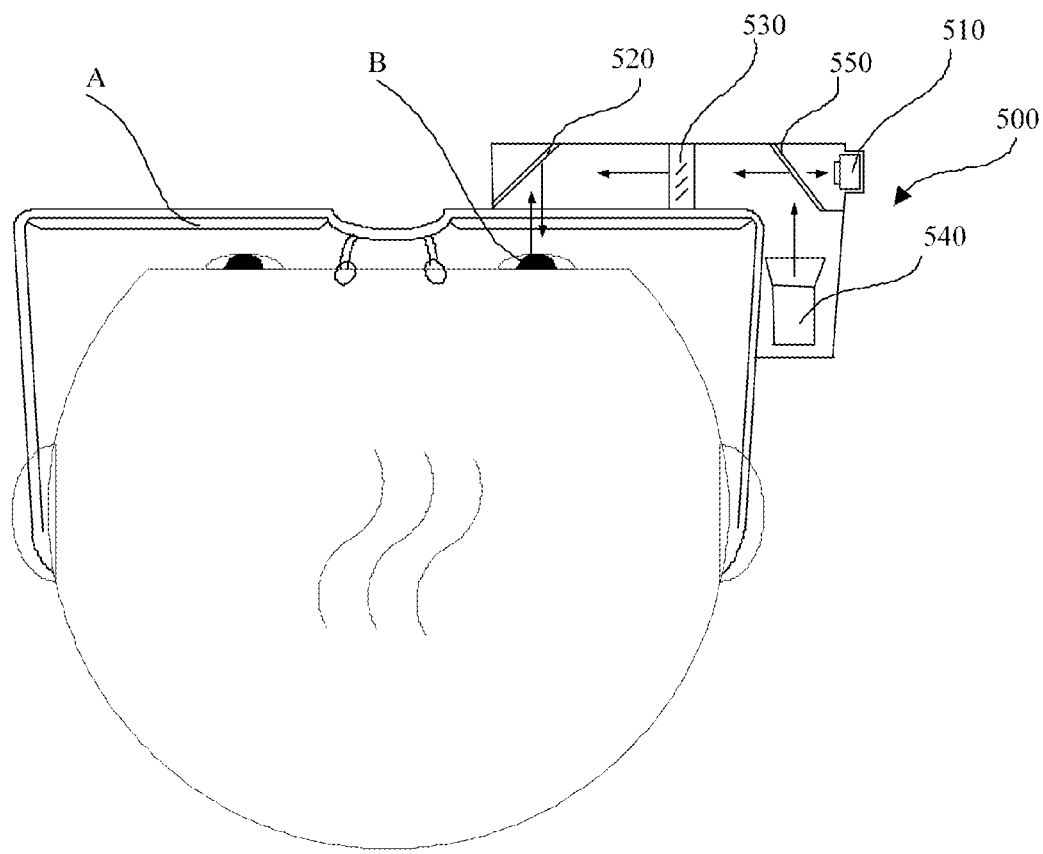
FIG. 5 is a schematic diagram in which an eye focusing point detection system of an information observation apparatus is applied to glasses according to an embodiment of the present application.

FIG. 5 shows an embodiment of applying a possible eye focusing point detection system 500 to a pair of glasses A (the glasses A may be the information observation apparatus in the embodiment of the present application), which comprises the content described in the implementation as shown in FIG. 4(b), and is specifically as follows: It can be seen from FIG. 5 that in this implementation, the system 500 of this implementation is integrated to the right side (the present invention is not limited thereto) of the glasses A, comprising:

a micro camera 510, having the same functions as the image collection device described in the implementation of FIG. 4(b), and arranged at the outer right side of an eye B in order not to affect the sightline of an observer normally viewing an object;

a first beam splitter 520, having the same functions as the beam splitting unit described in the implementation of FIG. 4(b), arranged with a certain tilt angle at the intersection point of the gaze direction of the eye B and the incident direction of the camera 510, and configured to transmit the light entering the eye B from an observed object and reflect the light from the eye to the camera 510; and a focal-length adjustable lens 530, having the same functions as the focal-length adjustable lens described in the implementation of FIG. 4(b), located between the first beam splitter 520 and the camera 510, and configured to adjust the focal length value in real time, so that the camera 510 can shoot a clearest image of the fundus at some focal length value.

In this implementation, the image processing device is not shown in FIG. 5, and has the same functions as the image processing device shown in FIG. 4(b).

Since the brightness of the fundus is not enough under normal circumstances, the fundus had better be illuminated, and in this implementation, the fundus is illuminated by a light emitting source 540. In order not to affect the experience of the observer, the light emitting source 540 herein can be preferably an eye-invisible light emitting source, and further, can preferably be a near-infrared light emitting source which does not much affect the eye B and to which the camera 510 is relatively sensitive.

In this implementation, the light emitting source 540 is located at the outer side of the right side of a glasses frame, so it needs a second beam splitter 550 together with the first beam splitter 520 to complete the transfer of the light emitted by the light emitting source 540 to the fundus. In this implementation, the second beam splitter 550 is also located in front of the incident surface of the camera 510, so it needs to transmit the light from the fundus to the second beam splitter 550.

It can be seen that in this implementation, in order to enhance the experience of the observer and enhance the capture definition of the camera 510, the first beam splitter 520 can have the characteristics of high reflectivity to infrared and high transmissivity to visible light. For example, an infrared reflective film can be arranged at the side, towards the eye B, of the first beam splitter 520 to achieve the characteristics described above.

It can be seen from FIG. 5 that since in this implementation, the eye focusing point detection system 500 is located at the side, away from the eye B, of the lens of the glasses A, the lens can also be considered as a part of the glasses during the calculation of the optical parameter of the eye, without needing to know the optical characteristics of the lens.

In other implementations of the embodiment of the present application, the eye focusing point detection system 500 may be located at the side, close to the eye B, of the lens of the glasses A, and then, it needs to obtain the optical characteristic parameters of the lens in advance and take the affecting factor of the lens into account when the distance of the focusing point is being calculated.

The light emitted by the light emitting source is reflected by the second beam splitter 550, transmitted by the focal-length adjustable lens 530, and reflected by the first beam splitter 520, then transmits through the lens of the glasses A to enter the eye of an observer, and finally arrives at the retina of the fundus; the camera 510 shoots an image of the fundus through the pupil of the eye B via an optical path formed of the first beam splitter 520, the focal-length adjustable lens 530, and the second beam splitter 550.

Figure 6:
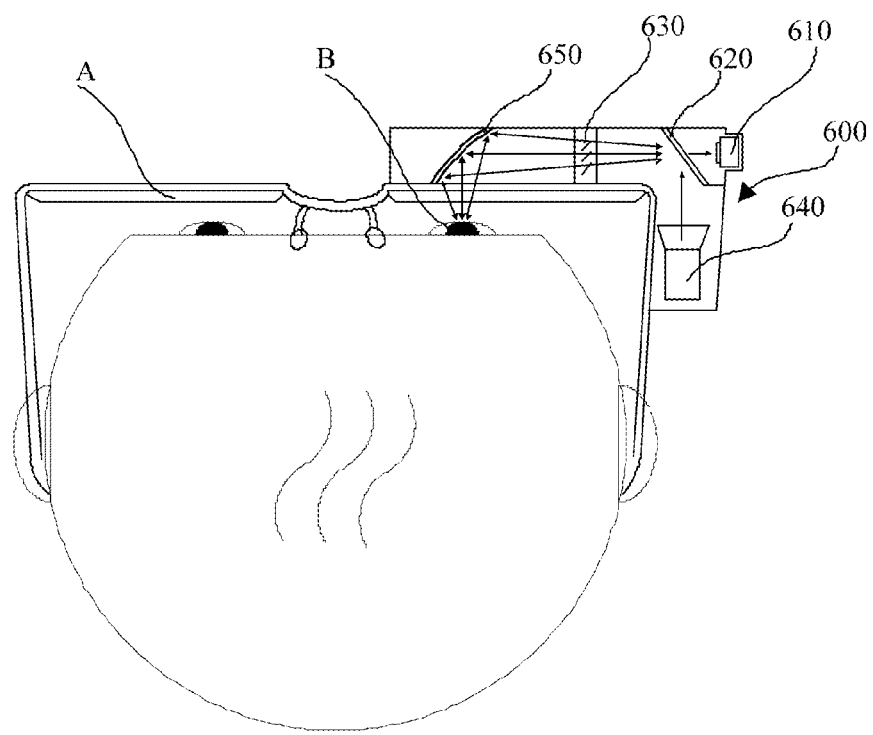
FIG. 6 is a schematic diagram in which an eye focusing point detection system of an information observation apparatus is applied to glasses according to an embodiment of the present application.

FIG. 6 is a schematic structural diagram of another eye focusing point detection system 600. It can be seen from FIG. 6 that this implementation is similar to the implementation shown in FIG. 5, comprising a micro camera 610, a second beam splitter 620, and a focal-length adjustable lens 630, except that the projection apparatus 640 in this implementation is a projection apparatus 640 configured to project a light spot pattern, and the first beam splitter in the implementation of FIG. 5 is replaced by a curved beam splitter 650 as a curved beam splitting unit.

The curved beam splitter 650 is adopted here to transfer, corresponding to a position of the pupil in a different optical axis direction of the eye, an image presented on the fundus to the image collection device. In this way, the camera can shoot the mixed and superimposed images formed of various angles of the eyeball; however, since only the fundus part through the pupil can clearly focus on the camera, while other parts will defocus and thereby fail clear focusing, the formed image of the fundus part will not be interfered severely, and the features of the fundus part can still be detected. Therefore, compared with the implementation shown in FIG. 5, this implementation can obtain an image of the fundus well in different gaze directions of an eye, so that the eye focusing point detection system of this implementation has a wider application range and higher detection precision.

Through the detection by any detection module 310 in the foregoing, when it is detected that the sightline focusing point of the observer moves out of an area corresponding to the observed object for a first preset period of time, the judgment module 320 judges that the sightline focusing point of the observer moves away from the observed object. The area corresponding to the observed object is preset; or may be set according to content of the observed object, for example, an area corresponding to a specific paragraph; or may also be set according to the area of the observed object; for example, for paper reading, the area may be a page, while for electronic reading, the area may be an display area of the electronic reading or a displayed page of the electronic reading. The first preset period of time may be set according to an actual situation, for example, according to a scenario in which the observer is and/or the size of the area of the observed object, and the like, so as to exclude a case in which the sightline focusing point moves outside the area of the observed object due to a subconscious action of the observer, for example, a blink, a transient head action, and the like.

When it is detected that the observed object changed, the judgment module 320 judges that the sightline focusing point of the observer moves away from the observed object. The switching of the observed object refers to a change, triggered by the observer or triggered automatically, of the observed object, and is, for example, page turning, page scrolling, and the like.

In the apparatus in the embodiment of the present application, when the position of the sightline focusing point of the observer falls within an area corresponding to the important information for a second preset period of time or a preset number of times, it may be judged that the observer has observed the corresponding important information. The second preset period of time and the preset number of times may also be set according to an actual situation, as long as a possibility that an unintentional sightline focusing point of the observer falls within the area corresponding to the important information is excluded.

In addition, still as shown in FIG. 3, the apparatus 300 in the embodiment of the present application may further comprise:

an identification module 340, configured to identify all important information in the observed object. The identification module 340 may identify the important information according to content of the observed object, for example, identify semantically content that needs special attention; or the observed object has visual features for the important information or the area corresponding to the important information, for example, a special sign for the important information or the area corresponding to the important information, a text, an image, a font, a color, a layout feature, and the like at this position, and the identification module 340 identifies the important information by using these visual features. The important information may also be identified according to metadata of the observed object. The metadata is data that describes data and an environment of the data. In the method in the embodiment of the present application, the metadata is description information of the observed object and may be generated in a process of generating the observed object, and the metadata describes which areas in the observed object comprise the important information. The metadata of the observed object can be obtained by the identification module 340.

To fully attract attention of the observer during observation, the apparatus 300 in the embodiment of the present application further comprises a marking module 350, configured to mark the important information, for example, mark the important information or the area corresponding to the important information through processing such as bold-facing, blackening, underlining, and highlighting of the corresponding area.

In addition, the apparatus 300 in the embodiment of the present application further comprises a labeling module 360, configured to: when or after the identification module 350 identifies the important information, label important information, which has been observed by the observer, in the observed object. Specifically, after the observer has observed a certain piece of important information and/or an area corresponding to the important information, the labeling module 360 may remove an original mark at the important information and/or the area corresponding to the important information, and label the important information and/or the area corresponding to the important information by using a visual mark different from the original mark. When no mark exists at the important information and/or the area corresponding to the important information, the important information and/or the area corresponding to the important information may further be labeled in a manner of labeling with a visual mark. In view of the above, when the observer finds that there is missed important information, the important information that has been observed can be filtered out more efficiently.

In addition, the reminding module 330 may remind the observer in one or several of the following manners: an audio manner, in which a reminder tone is output to remind the observer that there is important information that has not be viewed; a visual manner, in which the observer may be reminded in a manner (for example, flickering) visible to the observer that there is important information that has not be viewed, or the observer may be reminded more directly and efficiently by visually labeling (distinguished from a mark that has been made for the important information and/or the important information that has been observed) important information that has not been observed; a touch manner, for example, protrusion; a vibration manner; and a manner of restricting an operation of the observer, in which, specifically, when an observation behavior occurs on a device having a display function, the observer is reminded, in a manner of prohibiting the observer from scrolling or turning a page, and the like, that there is important information that has not be observed.

In sum, for the apparatus in the embodiment of the present application, a position of a sightline focusing point of an observer is detected accurately, and an observation behavior of the observer is detected according to a position of a focusing point, so that missing of important information can be radically prevented; in addition, all/observed/unobserved important information is labeled, so as to further improve efficiency of the observer to observe important information.

In addition, an embodiment of the present application further provides a computer readable media (or medium), comprising a computer readable instruction for, when being executed, performing the following operations: the operations in Step S110 to Step S130 in the foregoing method embodiment.

Figure 7:
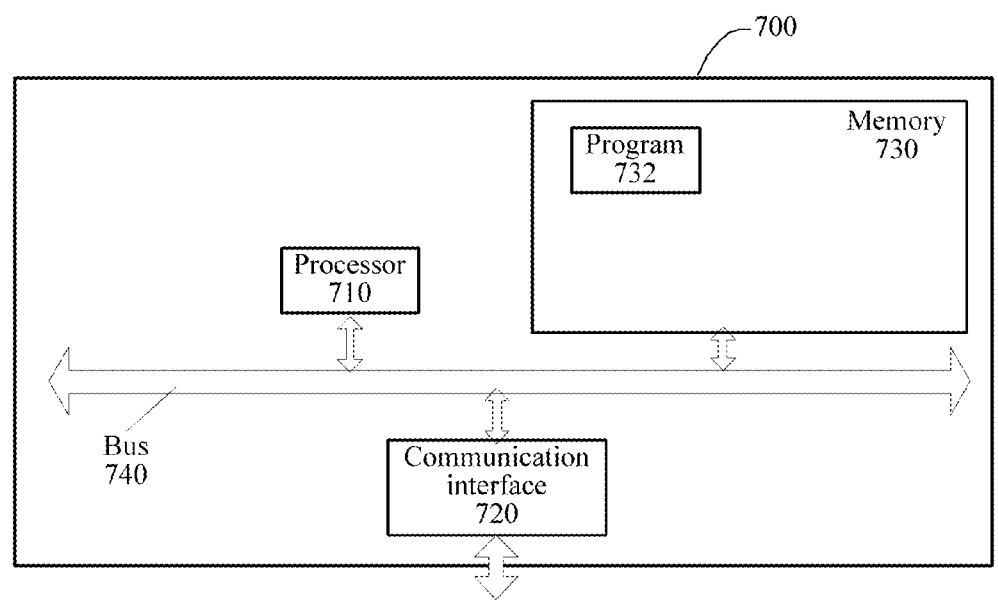
FIG. 7 is another schematic structural diagram of an information observation apparatus according to an embodiment of the present application.

FIG. 7 is a schematic structural diagram of an information observation apparatus 700 according to an embodiment of the present application. Specific embodiments of the present application do not cause a limitation on specific implementations of the information observation apparatus 700. As shown in FIG. 7, the information observation apparatus 700 may comprise:

a processor 710, a communication interface 720, a memory 730, and a communication bus 740, wherein:

the processor 710, the communication interface 720, and the memory 730 accomplish communication with each other through the communication bus 740;

the communication interface 720 is configured to communicate with a network element such as a client; and the processor 710 is configured to execute a program 732, and specifically can execute relevant steps in the foregoing method embodiment shown in the FIG. 1.

Specifically, the program 732 may comprise program code, and the program code comprises a computer operation instruction.

The processor 710 possibly is a central processing unit (CPU), or is an application specific integrated circuit (ASIC), or is configured to be one or more integrated circuits that implement the embodiments of the present application.

The memory 730 is configured to store the program 732. The memory 730 may comprise a high-speed random access memory (RAM) memory, and may also further comprise a non-volatile memory, for example, at least one magnetic disk memory. The program 732 specifically may cause the apparatus 700 to perform the following steps:

detecting a position of a sightline focusing point of an observer;

in response to that it is detected that the sightline focusing point of the observer moves away from an observed object, judging whether the observer has observed all important information on the observed object; and in response to that it is judged that the observer has not observed all important information in the observed object, reminding the observer.

For specific implementations of various units in the program 732, reference may be made to the corresponding steps or units on the embodiments of the present application, and details are not provided herein.

An embodiment of the present application further provides a wearable optical device, wherein the wearable optical device may be frame glasses shown in FIG. 5 or FIG. 6, or may also be contact lenses, and the wearable optical device comprises the information observation apparatus that is recorded in the foregoing embodiments.

In other possible implementations in the embodiment of the present application, the information observation apparatus possibly is further applied to another device relevant to an eye, for example, an unwearable optical device such as a telescope.

It can be appreciated by those skilled in the art that each exemplary unit and method step described with reference to the embodiments disclosed in this document can be achieved by electronic hardware or a combination of computer software and electronic hardware. Whether these functions are executed in a hardware mode or a software mode depends on the specific applications and design constraint conditions of the technical solution. Those professional technicians can use different methods to achieve the functions described with respect to each specific application, but this realization shall not be considered beyond the scope of the present application.

If the function is achieved in the form of a software functional unit and is sold or used as an independent product, it can be stored in a computer-readable storage medium. Based on such understanding, the technical solution of the present application essentially or the part which contributes to the prior art or a part of the technical solution can be embodied in the form of a software product, and the computer software product is stored in a storage medium, and comprises several instructions for enabling a computer apparatus (which can be a personal computer, a server, or a network device, and the like) to execute all or some steps of the method described in each embodiment of the present application. The preceding storage medium comprises various medium which can store a program code, such as a USB flash drive, a removable hard disk, a read-only memory (ROM), a RAM, a magnetic disk or an optical disc, and the like.

The above implementations are only used to describe the present application, without limiting the present application; various alterations and variations can be made by those skilled in the related art without departing from the spirit and scope of the present application, so all equivalent technical solutions also belong to the scope of the present application, and the scope of patent protection of the present application should be defined by claims.

What is claimed is:

1. An information observation method, wherein the method comprises:
    detecting a position of a sightline focusing point of an observer, wherein the detecting a position of a sightline focusing point of an observer comprises: capturing at least one image presented by a fundus of an eye of the observer; adjusting at least one imaging parameter of an optical path between the eye of the observer and a capture position, so as to capture at least one image that meets at least one predetermined definition standard; and according to the at least one imaging parameter of the optical path between the eye of the observer and the capture position in response to that the at least one image that meets the predetermined definition standard is captured and an optical parameter of the eye, calculating the position of the focusing point;
    in response to that it is detected that the sightline focusing point of the observer moves away from an observed object, judging whether the observer has observed important information on the observed object; and
    in response to that it is judged that the observer has not observed the important information on the observed object, reminding the observer.

2. The method according to claim 1, wherein the adjusting at least one imaging parameter of an optical path between the eye of the observer and a capture position comprises:
    adjusting the focal length of an optical component on the optical path between the eye of the observer and the capture position and/or a position of the optical component in the optical path.

3. The method according to claim 1, wherein the adjusting at least one imaging parameter of an optical path between the eye of the observer and a capture position, so as to capture at least one image that meets at least one predetermined definition standard comprises:
    according to positions of a pupil associated with different eye optical axis directions, transferring the at least one image presented by the fundus to the capture position respectively.

4. The method according to claim 1, wherein the in response to that it is detected that the sightline focusing point of the observer moves away from an observed object, judging whether the observer has observed important information on the observed object comprises:
    in response to that it is detected that the sightline focusing point of the observer moves out of an area corresponding to the observed object for a first preset period of time, judging that the sightline focusing point of the observer moves away from the observed object.

5. The method according to claim 1, wherein the in response to that it is detected that the sightline focusing point of the observer moves away from an observed object, judging whether the observer has observed important information on the observed object comprises:
    in response to that it is detected that the observed object changed, judging that the sightline focusing point of the observer moves away from the observed object.

6. The method according to claim 1, wherein the in response to that it is detected that the sightline focusing point of the observer moves away from an observed object, judging whether the observer has observed important information on the observed object comprises:
    in response to that it is detected that the position of the sightline focusing point of the observer falls within an area corresponding to important information for a second preset period of time, judging that the observer has observed the corresponding important information.

7. The method according to claim 1, wherein the in response to that it is detected that the sightline focusing point of the observer moves away from an observed object, judging whether the observer has observed important information on the observed object comprises:
    in response to that it is detected that the position of the sightline focusing point of the observer falls within an area corresponding to important information a preset number of times, judging that the observer has observed the corresponding important information.

8. The method according to claim 1, wherein the method further comprises:
    identifying the important information on the observed object.

9. The method according to claim 8, wherein the identifying the important information on the observed object comprises:
    identifying the important information on the observed object according to content of the observed object.

10. The method according to claim 8, wherein the identifying the important information on the observed object comprises:
    identifying the important information on the observed object according to metadata of the observed object.

11. The method according to claim 1, wherein the method further comprises:
    labeling important information that has been observed by the observer and/or an area corresponding to the important information.

12. A non-transitory computer readable storage medium, wherein the computer readable storage medium comprises an executable instruction, and when a central processing unit of an information observation apparatus executes the executable instruction, the executable instruction is configured to cause the information observation apparatus to execute the following method:
    detecting a position of a sightline focusing point of an observer, wherein the detecting a position of a sightline focusing point of an observer comprises: capturing at least one image presented by a fundus of an eye of the observer; adjusting at least one imaging parameter of an optical path between the eye of the observer and a capture position, so as to capture at least one image that meets at least one predetermined definition standard; and according to the at least one imaging parameter of the optical path between the eye of the observer and the capture position in response to that the at least one image that meets the predetermined definition standard is captured and an optical parameter of the eye, calculating the position of the focusing point;
    in response to that it is detected that the sightline focusing point of the observer moves away from an observed object, judging whether the observer has observed important information on the observed object; and
    in response to that it is judged that the observer has not observed the important information on the observed object, reminding the observer.

13. An information observation apparatus, comprising a central processing unit and a memory, wherein the memory stores a computer execution instruction, and the central processing unit is connected to the memory through a communication bus, and when the information observation apparatus runs, the central processing unit executes the computer execution instruction stored in the memory, to cause the information observation apparatus to execute the following method:
- detecting a position of a sightline focusing point of an observer, wherein the detecting a position of a sightline focusing point of an observer comprises: capturing at least one image presented by a fundus of an eye of the observer; adjusting at least one imaging parameter of an optical path between the eye of the observer and a capture position, so as to capture at least one image that meets at least one predetermined definition standard; and according to the at least one imaging parameter of the optical path between the eye of the observer and the capture position in response to that the at least one image that meets the predetermined definition standard is captured and an optical parameter of the eye, calculating the position of the focusing point;
- in response to that it is detected that the sightline focusing point of the observer moves away from an observed object, judging whether the observer has observed important information on the observed object; and
- in response to that it is judged that the observer has not observed the important information on the observed object, reminding the observer.

* * * * *